(12) United States Patent
Dugan et al.

(10) Patent No.: US 10,028,851 B2
(45) Date of Patent: *Jul. 24, 2018

(54) COATINGS FOR CONTROLLING EROSION OF A SUBSTRATE OF AN IMPLANTABLE MEDICAL DEVICE

(75) Inventors: Steve Dugan, San Francisco, CA (US); David C. Gale, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 2967 days.

This patent is subject to a terminal disclaimer.

(21) Appl. No.: 11/173,713

(22) Filed: Jun. 30, 2005

(65) Prior Publication Data

US 2005/0283229 A1   Dec. 22, 2005

Related U.S. Application Data

(60) Continuation-in-part of application No. 10/880,025, filed on Jun. 28, 2004, now Pat. No. 8,172,897, which is a continuation-in-part of application No. 10/767,296, filed on Jan. 28, 2004, now Pat. No. 7,699,890, which is a division of application No. 10/235,033, filed on Sep. 3, 2002, now Pat. No. 6,723,120, which is a continuation of application No. 09/797,313, filed on Mar. 1, 2001, now abandoned, (Continued)

(51) Int. Cl.
| | | |
|---|---|---|
| *A61F 2/06* | (2013.01) | |
| *A61F 2/915* | (2013.01) | |
| *A61F 2/91* | (2013.01) | |
| *A61L 31/10* | (2006.01) | |
| *A61L 31/14* | (2006.01) | |

(52) U.S. Cl.
CPC ............... *A61F 2/915* (2013.01); *A61F 2/91* (2013.01); *A61L 31/10* (2013.01); *A61L 31/146* (2013.01); *A61L 31/148* (2013.01); *A61F 2002/91533* (2013.01); *A61F 2230/0013* (2013.01); *A61F 2250/003* (2013.01); *A61F 2250/0019* (2013.01)

(58) Field of Classification Search
CPC .. A61F 2/915; A61F 2/91; A61F 2002/91533; A61F 2230/0013; A61F 2250/0019; A61F 2250/003; A61L 31/10; A61L 31/146; A61L 31/148; A61L 31/082
USPC ....... 623/1.15, 1.38, 1.42, 1.45, 1.46, 23.75; 506/1.15, 1.38
See application file for complete search history.

(56) References Cited

U.S. PATENT DOCUMENTS

| | | |
|---|---|---|
| 3,687,135 A | 8/1972 | Stroganov et al. |
| 3,839,743 A | 10/1974 | Schwarcz |
| 3,855,638 A | 12/1974 | Pilliar |

(Continued)

FOREIGN PATENT DOCUMENTS

| | | |
|---|---|---|
| DE | 44 07 079 | 9/1994 |
| DE | 197 31 021 | 1/1999 |

(Continued)

OTHER PUBLICATIONS

U.S. Appl. No. 10/317,435, filed Dec. 11, 2002, Hossainy et al.

(Continued)

*Primary Examiner* — Jing Ou
(74) *Attorney, Agent, or Firm* — Squire Patton Boggs (US) LLP

(57) ABSTRACT

An implantable medical device, such as a stent, with a coating region for controlling erosion of the substrate region is disclosed.

2 Claims, 3 Drawing Sheets

Related U.S. Application Data which is a division of application No. 08/837,993, filed on Apr. 15, 1997, now Pat. No. 6,240,616.

(56) References Cited

U.S. PATENT DOCUMENTS

| | | |
|---|---|---|
| 3,900,632 A | 8/1975 | Robinson |
| 4,101,984 A | 7/1978 | MacGregor |
| 4,104,410 A | 8/1978 | Malecki |
| 4,110,497 A | 8/1978 | Hoel |
| 4,321,711 A | 3/1982 | Mano |
| 4,346,028 A | 8/1982 | Griffith |
| 4,355,426 A | 10/1982 | MacGregor |
| 4,374,669 A | 2/1983 | MacGregor |
| 4,405,319 A * | 9/1983 | Cosentino ............ 604/175 |
| 4,458,366 A | 7/1984 | MacGregor |
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |
| 4,693,721 A | 9/1987 | Ducheyne |
| 4,718,907 A | 1/1988 | Karwoski et al. |
| 4,722,335 A | 2/1988 | Vilasi |
| 4,723,549 A | 2/1988 | Wholey et al. |
| 4,729,871 A | 3/1988 | Morimoto |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,902,289 A | 2/1990 | Yannas |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,078,736 A * | 1/1992 | Behl ............ 623/1.15 |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A * | 11/1992 | Pinchuk ............ 623/23.49 |
| 5,167,614 A | 12/1992 | Tessmann et al. |
| 5,171,262 A | 12/1992 | MacGregor |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,370,682 A | 12/1994 | Schmitt |
| 5,370,684 A | 12/1994 | Vallana et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,419,760 A | 5/1995 | Narciso, Jr. |
| 5,423,885 A | 6/1995 | Williams |
| 5,433,909 A | 7/1995 | Marakos et al. |
| 5,437,834 A | 8/1995 | Okimatsu et al. |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. |
| 5,477,864 A | 12/1995 | Davidson |
| 5,492,768 A | 2/1996 | Okimatsu et al. |
| 5,502,158 A | 3/1996 | Sinclair et al. |
| 5,514,379 A | 5/1996 | Weissleder et al. |
| 5,518,730 A | 5/1996 | Fuisz |
| 5,522,894 A | 6/1996 | Draenert |
| 5,527,337 A | 6/1996 | Stack et al. |
| 5,540,712 A | 7/1996 | Kleshinski et al. |
| 5,545,408 A | 8/1996 | Trigg et al. |
| 5,554,120 A | 9/1996 | Chen et al. |
| 5,556,413 A | 9/1996 | Lam |
| 5,571,187 A | 11/1996 | Devanathan |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,693 A | 2/1997 | Seare, Jr. |
| 5,605,696 A | 2/1997 | Eury et al. |
| 5,607,442 A | 3/1997 | Fischell et al. |
| 5,607,463 A | 3/1997 | Schwartz et al. |
| 5,607,467 A | 3/1997 | Froix |
| 5,618,299 A | 4/1997 | Khosravi et al. |
| 5,624,411 A | 4/1997 | Tuch |
| 5,629,077 A | 5/1997 | Turnlund et al. |
| 5,630,840 A | 5/1997 | Mayer |
| 5,631,135 A | 5/1997 | Gryaznov et al. |
| 5,632,771 A | 5/1997 | Boatman et al. |
| 5,632,779 A | 5/1997 | Davidson |
| 5,632,840 A | 5/1997 | Campbell |
| 5,637,113 A | 6/1997 | Tartaglia et al. |
| 5,641,443 A | 6/1997 | Calcote et al. |
| 5,649,977 A | 7/1997 | Campbell |
| 5,667,767 A | 9/1997 | Greff et al. |
| 5,667,796 A | 9/1997 | Otten |
| 5,670,558 A | 9/1997 | Onishi et al. |
| 5,693,085 A | 12/1997 | Buirge et al. |
| 5,697,967 A | 12/1997 | Dinh et al. |
| 5,700,286 A | 12/1997 | Tartaglia et al. |
| 5,707,385 A | 1/1998 | Williams |
| 5,711,763 A | 1/1998 | Nonami et al. |
| 5,713,949 A | 2/1998 | Jayaraman |
| 5,716,981 A | 2/1998 | Hunter et al. |
| 5,725,549 A | 3/1998 | Lam |
| 5,725,567 A | 3/1998 | Wolff et al. |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,746,691 A | 5/1998 | Frantzen |
| 5,755,771 A | 5/1998 | Penn et al. |
| 5,756,457 A | 5/1998 | Wang et al. |
| 5,756,476 A | 5/1998 | Epstein et al. |
| 5,759,192 A | 6/1998 | Saunders |

(56) References Cited

U.S. PATENT DOCUMENTS

| | | | |
|---|---|---|---|
| 5,765,682 | A | 6/1998 | Bley et al. |
| 5,766,204 | A | 6/1998 | Porter et al. |
| 5,766,239 | A | 6/1998 | Cox |
| 5,766,710 | A | 6/1998 | Turnlund et al. |
| 5,769,883 | A | 6/1998 | Buscemi et al. |
| 5,769,884 | A | 6/1998 | Solovay |
| 5,780,807 | A | 7/1998 | Saunders |
| 5,788,558 | A | 8/1998 | Klein |
| 5,800,512 | A | 9/1998 | Lentz et al. |
| 5,800,516 | A | 9/1998 | Fine et al. |
| 5,811,447 | A | 9/1998 | Kunz et al. |
| 5,824,049 | A | 10/1998 | Ragheb et al. |
| 5,830,178 | A | 11/1998 | Jones et al. |
| 5,830,461 | A | 11/1998 | Billiar |
| 5,830,879 | A | 11/1998 | Isner |
| 5,833,651 | A | 11/1998 | Donovan et al. |
| 5,834,582 | A | 11/1998 | Sinclair et al. |
| 5,836,962 | A | 11/1998 | Gianotti |
| 5,837,313 | A | 11/1998 | Ding et al. |
| 5,837,835 | A | 11/1998 | Gryaznov et al. |
| 5,840,083 | A | 11/1998 | Braach-Maksvytis |
| 5,843,172 | A | 12/1998 | Yan |
| 5,851,508 | A | 12/1998 | Greff et al. |
| 5,853,408 | A | 12/1998 | Muni |
| 5,854,207 | A | 12/1998 | Lee et al. |
| 5,855,612 | A | 1/1999 | Ohthuki et al. |
| 5,855,618 | A | 1/1999 | Patnaik et al. |
| 5,856,814 | A | 1/1999 | Yagyu |
| 5,858,746 | A | 1/1999 | Hubbell et al. |
| 5,865,814 | A | 2/1999 | Tuch |
| 5,868,781 | A | 2/1999 | Killion |
| 5,873,904 | A | 2/1999 | Ragheb et al. |
| 5,874,101 | A | 2/1999 | Zhong et al. |
| 5,874,109 | A | 2/1999 | Ducheyne et al. |
| 5,874,165 | A | 2/1999 | Drumheller |
| 5,876,743 | A | 3/1999 | Ibsen et al. |
| 5,877,263 | A | 3/1999 | Patnaik et al. |
| 5,879,398 | A | 3/1999 | Swarts et al. |
| 5,879,713 | A | 3/1999 | Roth et al. |
| 5,888,533 | A | 3/1999 | Dunn |
| 5,891,192 | A | 4/1999 | Murayama et al. |
| 5,897,955 | A | 4/1999 | Drumheller |
| 5,906,759 | A | 5/1999 | Richter |
| 5,914,182 | A | 6/1999 | Drumheller |
| 5,916,584 | A | 6/1999 | O'Donoghue |
| 5,916,870 | A | 6/1999 | Lee et al. |
| 5,922,005 | A | 7/1999 | Richter et al. |
| 5,942,209 | A | 8/1999 | Leavitt et al. |
| 5,945,029 | A | 8/1999 | Scholz et al. |
| 5,948,428 | A | 9/1999 | Lee et al. |
| 5,954,744 | A | 9/1999 | Phan et al. |
| 5,957,975 | A | 9/1999 | Lafont et al. |
| 5,965,720 | A | 10/1999 | Gryaznov et al. |
| 5,971,954 | A | 10/1999 | Conway et al. |
| 5,972,027 | A * | 10/1999 | Johnson ............... 623/1.42 |
| 5,976,182 | A | 11/1999 | Cox |
| 5,980,564 | A | 11/1999 | Stinson |
| 5,980,928 | A | 11/1999 | Terry |
| 5,980,972 | A | 11/1999 | Ding |
| 5,981,568 | A | 11/1999 | Kunz et al. |
| 5,986,169 | A | 11/1999 | Gjunter |
| 5,997,468 | A | 12/1999 | Wolff et al. |
| 6,010,445 | A | 1/2000 | Armini et al. |
| 6,010,529 | A | 1/2000 | Herweck et al. |
| 6,015,541 | A | 1/2000 | Greff et al. |
| 6,027,779 | A | 2/2000 | Campbell et al. |
| 6,033,582 | A | 3/2000 | Lee et al. |
| 6,042,875 | A | 3/2000 | Ding et al. |
| 6,048,964 | A | 4/2000 | Lee et al. |
| 6,051,648 | A | 4/2000 | Rhee et al. |
| 6,056,993 | A | 5/2000 | Leidner et al. |
| 6,060,451 | A | 5/2000 | DiMaio et al. |
| 6,066,156 | A | 5/2000 | Yan |
| 6,071,266 | A | 6/2000 | Kelley |
| 6,074,659 | A | 6/2000 | Kunz et al. |
| 6,080,177 | A | 6/2000 | Igaki et al. |
| 6,080,488 | A | 6/2000 | Hostettler et al. |
| 6,083,258 | A | 7/2000 | Yadav |
| 6,093,463 | A | 7/2000 | Thakrar |
| 6,095,817 | A | 8/2000 | Wagner et al. |
| 6,096,070 | A | 8/2000 | Ragheb et al. |
| 6,096,525 | A | 8/2000 | Patnaik |
| 6,099,562 | A | 8/2000 | Ding et al. |
| 6,103,230 | A | 8/2000 | Billiar et al. |
| 6,107,416 | A | 8/2000 | Patnaik et al. |
| 6,110,188 | A | 8/2000 | Narciso, Jr. |
| 6,113,629 | A | 9/2000 | Ken |
| 6,117,979 | A | 9/2000 | Hendriks et al. |
| 6,120,536 | A | 9/2000 | Ding et al. |
| 6,120,904 | A | 9/2000 | Hostettler et al. |
| 6,121,027 | A | 9/2000 | Clapper et al. |
| 6,125,523 | A | 10/2000 | Brown et al. |
| 6,127,173 | A | 10/2000 | Eckstein et al. |
| 6,129,761 | A | 10/2000 | Hubbell |
| 6,129,928 | A | 10/2000 | Sarangapani et al. |
| 6,143,370 | A | 11/2000 | Panagiotou et al. |
| 6,150,630 | A | 11/2000 | Perry et al. |
| 6,153,252 | A | 11/2000 | Hossainy et al. |
| 6,159,951 | A | 12/2000 | Karpeisky et al. |
| 6,160,084 | A | 12/2000 | Langer et al. |
| 6,165,210 | A | 12/2000 | Lau et al. |
| 6,165,212 | A | 12/2000 | Dereume et al. |
| 6,166,130 | A | 12/2000 | Rhee et al. |
| 6,169,170 | B1 | 1/2001 | Gryaznov et al. |
| 6,171,609 | B1 | 1/2001 | Kunz |
| 6,174,330 | B1 | 1/2001 | Stinson |
| 6,177,523 | B1 | 1/2001 | Reich et al. |
| 6,183,505 | B1 | 2/2001 | Mohn, Jr. et al. |
| 6,187,045 | B1 | 2/2001 | Fehring et al. |
| 6,210,715 | B1 | 4/2001 | Starling et al. |
| 6,224,626 | B1 | 5/2001 | Steinke |
| 6,228,845 | B1 | 5/2001 | Donovan et al. |
| 6,240,616 | B1 | 6/2001 | Yan |
| 6,245,076 | B1 | 6/2001 | Yan |
| 6,245,103 | B1 | 6/2001 | Stinson |
| 6,248,344 | B1 | 6/2001 | Ylanen et al. |
| 6,251,135 | B1 | 6/2001 | Stinson et al. |
| 6,251,142 | B1 | 6/2001 | Bernacca et al. |
| 6,273,913 | B1 | 8/2001 | Wright et al. |
| 6,281,262 | B1 | 8/2001 | Shikinami |
| 6,284,333 | B1 | 9/2001 | Wang et al. |
| 6,287,332 | B1 | 9/2001 | Bolz et al. |
| 6,287,337 | B1 | 9/2001 | Martakos et al. |
| 6,290,721 | B1 | 9/2001 | Heath |
| 6,293,966 | B1 | 9/2001 | Frantzen |
| 6,303,901 | B1 | 10/2001 | Perry et al. |
| 6,312,459 | B1 | 11/2001 | Huang et al. |
| 6,327,772 | B1 | 12/2001 | Zadno-Azizi et al. |
| 6,375,826 | B1 | 4/2002 | Wang et al. |
| 6,379,381 | B1 | 4/2002 | Hossainy et al. |
| 6,387,121 | B1 | 5/2002 | Alt |
| 6,388,043 | B1 | 5/2002 | Langer et al. |
| 6,395,326 | B1 | 5/2002 | Castro et al. |
| 6,409,761 | B1 | 6/2002 | Jang |
| 6,423,092 | B2 | 7/2002 | Datta et al. |
| 6,461,632 | B1 | 10/2002 | Gogolewski |
| 6,464,720 | B2 | 10/2002 | Boatman et al. |
| 6,479,565 | B1 | 11/2002 | Stanley |
| 6,485,512 | B1 | 11/2002 | Cheng |
| 6,492,615 | B1 | 12/2002 | Flanagan |
| 6,494,908 | B1 | 12/2002 | Huxel et al. |
| 6,495,156 | B2 | 12/2002 | Wenz et al. |
| 6,511,748 | B1 | 1/2003 | Barrows |
| 6,517,888 | B1 | 2/2003 | Weber |
| 6,527,801 | B1 | 3/2003 | Dutta |
| 6,537,589 | B1 | 3/2003 | Chae et al. |
| 6,539,607 | B1 | 4/2003 | Fehring et al. |
| 6,540,777 | B2 | 4/2003 | Stenzel |
| 6,554,854 | B1 | 4/2003 | Flanagan |
| 6,565,599 | B1 | 5/2003 | Hong et al. |
| 6,569,191 | B1 | 5/2003 | Hogan |
| 6,569,193 | B1 | 5/2003 | Cox et al. |
| 6,572,672 | B2 | 6/2003 | Yadav et al. |
| 6,574,851 | B1 | 6/2003 | Mirizzi |

(56) References Cited

U.S. PATENT DOCUMENTS

| | | |
|---|---|---|
| 6,585,755 B2 | 7/2003 | Jackson et al. |
| 6,592,614 B2 | 7/2003 | Lenker et al. |
| 6,592,617 B2 | 7/2003 | Thompson |
| 6,610,087 B1 | 8/2003 | Zarbatany et al. |
| 6,613,072 B2 | 9/2003 | Lau et al. |
| 6,626,939 B1 | 9/2003 | Burnside et al. |
| 6,635,269 B1 | 10/2003 | Jennissen |
| 6,645,243 B2 | 11/2003 | Vallana et al. |
| 6,656,162 B2 | 12/2003 | Santini, Jr. et al. |
| 6,664,335 B2 | 12/2003 | Krishnan |
| 6,666,214 B2 | 12/2003 | Canham |
| 6,667,049 B2 | 12/2003 | Janas et al. |
| 6,669,723 B2 | 12/2003 | Killion et al. |
| 6,676,697 B1 | 1/2004 | Richter |
| 6,679,980 B1 | 1/2004 | Andreacchi |
| 6,689,375 B1 | 2/2004 | Wahlig et al. |
| 6,695,920 B1 | 2/2004 | Pacetti et al. |
| 6,706,273 B1 | 3/2004 | Roessler |
| 6,709,379 B1 | 3/2004 | Brandau et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,723,120 B2 | 4/2004 | Yan |
| 6,746,773 B2 | 6/2004 | Llanos et al. |
| 6,752,826 B2 | 6/2004 | Holloway et al. |
| 6,753,007 B2 | 6/2004 | Haggard et al. |
| 6,764,505 B1 | 7/2004 | Hossainy et al. |
| 6,818,063 B1 | 11/2004 | Kerrigan |
| 6,846,323 B2 | 1/2005 | Yip et al. |
| 6,867,248 B1 | 3/2005 | Martin et al. |
| 7,011,678 B2 * | 3/2006 | Tenerz et al. ............... 623/1.15 |
| 2001/0013166 A1 * | 8/2001 | Yan ........................... 29/527.2 |
| 2001/0044652 A1 | 11/2001 | Moore |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0038145 A1 | 3/2002 | Jang |
| 2002/0045668 A1 * | 4/2002 | Dang et al. ................. 514/649 |
| 2002/0062148 A1 | 5/2002 | Hart |
| 2002/0065553 A1 | 5/2002 | Weber |
| 2002/0082679 A1 | 6/2002 | Sirhan et al. |
| 2002/0111590 A1 | 8/2002 | Davila et al. |
| 2002/0116050 A1 | 8/2002 | Kocur |
| 2002/0138133 A1 | 9/2002 | Lenz et al. |
| 2002/0161114 A1 | 10/2002 | Gunatillake et al. |
| 2002/0165601 A1 | 11/2002 | Clerc |
| 2003/0033001 A1 | 2/2003 | Igaki |
| 2003/0093107 A1 | 5/2003 | Parsonage et al. |
| 2003/0100865 A1 | 5/2003 | Santini, Jr. et al. |
| 2003/0105518 A1 | 6/2003 | Dutta |
| 2003/0105530 A1 | 6/2003 | Pirhonen |
| 2003/0153972 A1 | 8/2003 | Helmus |
| 2003/0171053 A1 | 9/2003 | Sanders |
| 2003/0187495 A1 | 10/2003 | Cully et al. |
| 2003/0208259 A1 | 11/2003 | Penhasi |
| 2003/0209835 A1 | 11/2003 | Chun et al. |
| 2003/0226833 A1 | 12/2003 | Shapovalov et al. |
| 2003/0236565 A1 | 12/2003 | Fifer |
| 2004/0034409 A1 | 2/2004 | Heublein et al. |
| 2004/0088038 A1 | 5/2004 | Dehnad et al. |
| 2004/0093077 A1 | 5/2004 | White et al. |
| 2004/0098095 A1 | 5/2004 | Burnside et al. |
| 2004/0111149 A1 | 6/2004 | Stinson |
| 2004/0127970 A1 | 7/2004 | Weber |
| 2004/0143317 A1 | 7/2004 | Stinson et al. |
| 2004/0167610 A1 | 8/2004 | Fleming, III |
| 2005/0079200 A1 * | 4/2005 | Rathenow ............ A61L 27/303 424/423 |
| 2005/0209680 A1 | 9/2005 | Gale et al. |
| 2005/0261760 A1 | 11/2005 | Weber |
| 2005/0266040 A1 * | 12/2005 | Gerberding .......... A61K 31/337 424/423 |
| 2006/0052824 A1 * | 3/2006 | Ransick ............. A61B 17/0644 606/219 |
| 2006/0229711 A1 | 10/2006 | Yan et al. |
| 2006/0271168 A1 | 11/2006 | Kleine et al. |
| 2009/0306765 A1 * | 12/2009 | Weber ..................... A61F 2/91 623/1.15 |

FOREIGN PATENT DOCUMENTS

| | | |
|---|---|---|
| DE | 198 56 983 | 12/1999 |
| DE | 103 57 747 | 1/2005 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 687 008 | 12/1995 |
| EP | 0 709 068 | 5/1996 |
| EP | 0 970 711 | 1/2000 |
| EP | 1 362 603 | 11/2003 |
| GB | 2 247 696 | 3/1992 |
| JP | 63-160645 | 7/1988 |
| JP | 3-14516 | 1/1991 |
| JP | 4-215768 | 8/1992 |
| JP | 8-33718 | 2/1996 |
| JP | 8-213026 | 8/1996 |
| JP | 9-85028 | 3/1997 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/13268 | 6/1994 |
| WO | WO 94/21196 | 9/1994 |
| WO | WO 95/11817 | 5/1995 |
| WO | WO 95/29647 | 11/1995 |
| WO | WO 96/28115 | 9/1996 |
| WO | WO 98/04415 | 2/1998 |
| WO | WO 98/23228 | 6/1998 |
| WO | WO 98/56312 | 12/1998 |
| WO | WO 99/03515 | 1/1999 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 03/063733 | 8/2003 |
| WO | WO 2004/023985 | 3/2004 |

OTHER PUBLICATIONS

Anonymous, *Bioabsorbable stent mounted on a catheter having optical coherence tomography capabilities*, Research Disclosure, Sep. 2004, pp. 1159-1162.

Ansari, *End-to-end tubal anastomosis using an absorbable stent*, Fertility and Sterility, vol. 32(2), pp. 197-201 (Aug. 1979).

Ansari, *Tubal Reanastomosis Using Absorbable Stent*, International Journal of Fertility, vol. 23, No. 4, pp. 242-243 (1978).

Bull, *Parylene Coating for Medical Applications*, Medical Product Manufacturing News 18,1 pg. (Mar. 1993).

Casper et al., *Fiber-Reinforced Absorbable Composite for Orthopedic Surgery*, Polymeric Materials Science and Engineering, 53: pp. 497-501 (1985).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).

(56) References Cited

OTHER PUBLICATIONS

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).
Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).
Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).
Devanathan et al., *Polymeric Conformal Coatings for Implantable Electronic Devices*, IEEE Transactions on Biomedical Engineering, vol. BME-27(11), pp. 671-675 (1980).
Elbert et al., *Conjugate Addition Reactions Combined with Free-Radical Cross-Linking for the Design of Materials for Tissue Engineering*, Biomacromolecules 2, pp. 430-441 (2001).
Hahn et al., *Biocompatibility of Glow-Discharge-Polymerized Films and Vacuum-Deposited Parylene*, J Applied Polymer Sci, 38, pp. 55-64 (1984).
Hahn et al., *Glow Discharge Polymers as Coatings for Implanted Devices*, ISA, pp. 109-111 (1981).
He et al., *Assessment of Tissue Blood Flow Following Small Artery Welding with an Intraluminal Dissolvable Stent*, Microsurgery, vol. 19(3), pp. 148-152 (1999).
Kelley et al., *Totally Resorbable High-Strength Composite Material*, Advances in Biomedical Polymers, 35, pp. 75-85 (1987).
Kubies et al., *Microdomain Structure in polylactide-block-poly(ethylene oxide) copolymer films*, Biomaterials 21, pp. 529-536 (2000).
Kutryk et al., *Coronary Stenting: Current Perspectives*, a companion to the Handbook of Coronary Stents pp. 1-16 (1999).
Martin et al., *Enhancing the biological activity of immobilized osteopontin using a type-1 collagen affinity coating*, J. Biomed. Mater Res 70A, pp. 10-19 (2004).
Mauduit et al., *Hydrolytic degradation of films prepared from blends of high and low moledular weight poly(DL-lactic acid)s*, J. Biomed. Mater. Res. v. 30, pp. 201-207 (1996).
Middleton et al., *Synthetic biodegradable polymers as orthopedic devices*, Biomaterials, vol. 21, pp. 2335-2346 (2000).
Muller et al., *Advances in Coronary Angioplasty: Endovascular Stents*, Coron. Arter. Dis., 1(4), pp. 438-448 (Jul./Aug. 1990).
Nichols et al., *Electrical Insulation of Implantable Devices by Composite Polymer Coatings*, ISA Transactions, 26(4), pp. 15-18 (1987).
Peuster et al., *A novel approach to temporary stenting: degradable cardiovascular stents produced from corrodible metal-results 6-18 months after implantation into New Zealand white rabbits*, Heart 86, pp. 563-569 (2001).
Pietrzak et al., *Bioabsorbable Fixation Devices: Status for the Craniomaxillofacial Surgeon*, J. Craniofaxial Surg. 2, pp. 92-96 (1997).
Pietrzak et al., *Bioresorbable implants—practical considerations*, Bone v. 19, No. 1, Supplement Jul. 1996: 109S-119S.
Redman, *Clinical Experience with Vasovasostomy Utilizing Absorbable Intravasal Stent*, Urology, vol. 20(1), pp. 59-61 (Jul. 1982).
Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).
Schatz, *A View of Vascular Stents*, Circulation, 79(2), pp. 445-457 (Feb. 1989).
Schmidt et al., *Long-Term Implants of Parylene-C Coated Microelectrodes*, Med & Biol Eng & Comp, 26(1), pp. 96-101 (Jan. 1988).
Spagnuolo et al., *Gas 1 is induced by VE-cadherin and vascular endothelial growth factor and inhibits endothelial cell apoptosis*, Blood 103, pp. 3005-3012 (2004).
Tamai et al., *Initial and 6-Month Results of Biodegradable Poly-l-Lactic Acid Coronary Stents in Humans*, Circulation, pp. 399-404 (Jul. 25, 2000).
Tsuji et al., *Biodegradable Polymeric Stents*, Current Interventional Cardiology Reports 3, pp. 10-17 (2001).
Völkel et al., *Targeting of immunoliposomes to endothelial cells using a single-chain Fv fragment directed against human endoglin (CD105)*, Biochimica et Biophysica Acta 1663, pp. 158-166 (2004).
von Recum et al., *Degradation of polydispersed poly(L-lactic acid) to modulate lactic acid release*, Biomaterials 16, pp. 441-445 (1995).
Yau et al., *Modern Size-Exclusion Liquid Chromatography*, Wiley-Interscience Publication, IX-XV (1979).
Search Report for PCT/US2006/025937 filed Jun. 30, 2006, dated Nov. 9, 2006, 18 pgs.
International Search Report for PCT/US2007/011177, dated Aug. 11, 2008, 13 pgs.
De Scheerder et al., *Biocompatibility of Polymer-Coated Oversized Metallic Stents Implanted in Normal Porcine Coronary Arteries*, Atherosclerosis 114:105-114 (1995).
Feng-Chun et al., *Assessment of Tissue Blood Flow Following Small Artery Welding with an Intraluminal Dissolvable Stent*, Microsurgery, vol. 19(3), pp. 148-152 (1999).
Lambert et al., *Localized Arterial Wall Drug Delivery From a Polymer-Coated Removable Metallic Stent*, Circulation 90(2):1003-1011 (Aug. 1994).
*Properties and Selection: Nonferrous Alloys and Special-Purpose Materials*, taken from: Housh S., Mikucki B. ASM Handbook vol. 2, last udated Oct. 24, 2008, Web Article: http://mg.tripod.com/asm_prop.htm.
Song et al., *Electrodeposition of hydroxyapatite coating on AZ91D magnesium alloy for biomaterial application*, Mat. Let. 62, pp. 3276-3279 (2008).
Lambert et al., *Localized Arterial Wall Drug Delivery From a Polymer-Coated Removable Metallic Stent*, Circulation 90(2)1003-1011 (Aug. 1994).

\* cited by examiner

COATINGS FOR CONTROLLING EROSION OF A SUBSTRATE OF AN IMPLANTABLE MEDICAL DEVICE

CROSS-REFERENCE

This is a continuation-in-part of application Ser. No. 10/880,025 filed on Jun. 28, 2004, now U.S. Pat. No. 8,172,897, which is a continuation-in-part of application Ser. No. 10/767,296 filed on Jan. 28, 2004, now U.S. Pat. No. 7,699,890, which is a divisional application of application Ser. No. 10/235,033, which was filed on Sep. 3, 2002, and issued on Apr. 20, 2004, as U.S. Pat. No. 6,723,120 which is a continuation of application Ser. No. 09/797,313, filed on Mar. 1, 2001, abandoned on Oct. 11, 2002, which is a division of application Ser. No. 08/837,993, filed on Apr. 15, 1997, and issued Jun. 5, 2001 as U.S. Pat. No. 6,240,616.

BACKGROUND OF THE INVENTION

Field of the Invention

This invention relates to implantable medical devices, such as stents, that have coatings that control erosion of bioabsorbable substrates of the devices.

Description of the State of the Art

This invention relates generally to implantable medical devices having a range of mechanical and therapeutic requirements during use. In particular, the invention relates to radially expandable endoprostheses that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty or valvuloplasty) with apparent success.

Plaques have been associated with stenosis and restenosis. While treatments of plaque-induced stenosis and restenosis have advanced significantly over the last few decades, the morbidity and mortality associated with vascular plaques have remained significant. Recent work suggests that plaque may generally fall into one of two different general types: standard stenotic plaques and vulnerable plaques. Stenotic plaque, which is sometimes referred to as thrombosis-resistant plaque, can generally be treated effectively by the known intravascular lumen opening techniques. Although plaques induce stenosis, these atherosclerotic plaques themselves are often a benign and are an effectively treatable disease.

Unfortunately, as plaque matures, narrowing of a blood vessel by a proliferation of smooth muscle cells, matrix synthesis, and lipid accumulation may result in formation of a plaque which is quite different than a standard stenotic plaque. Such atherosclerotic plaque becomes thrombosis-prone, and can be highly dangerous. This thrombosis-prone or vulnerable plaque may be a frequent cause of acute coronary syndrome. Both restenosis and vulnerable plaque may be treated by administering to a patient an active agent or a suitable combination of active agents through the use of an implantable medical device, such as a stent.

The treatment of a diseased site or lesion with a stent involves both delivery and deployment of the stent. "Delivery" refers to introducing and transporting the stent, through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen. In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn allowing the stent to self-expand.

Stents have been made of many materials including metals and polymers. Polymer materials include both biostable and biodegradable polymer materials. Metallic stents are typically formed from biostable metals. Bioerodible metal stents have been described previously. U.S. Pat. No. 6,287,332 B1 to Bolz et al., U.S. Pat. Appl. Pub. Ser. No. 2002/0004060 A1 to Heublein et. al.

The stent must be able to satisfy several mechanical requirements. First, the stent must be capable of withstanding the structural loads, namely radial compressive forces, imposed on the stent as it supports the walls of a vessel lumen. This requires a sufficient degree of strength and rigidity or stiffness. In addition to having adequate radial strength or more accurately, hoop strength, the stent should be longitudinally flexible to allow it to be maneuvered through a tortuous vascular path and to enable it to conform to a deployment site that may not be linear or may be subject to flexure. The material from which the stent is constructed must allow the stent to undergo expansion which typically requires substantial deformation of localized portions of the stent's structure. Once expanded, the stent must maintain its size and shape throughout its service life despite the various forces that may come to bear thereon, including the cyclic loading induced by the beating heart. Therefore, a stent must be capable of exhibiting relatively high toughness which corresponds to high strength and rigidity, as well as flexibility.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodible materials such as bioabsorbable polymers should be configured to completely erode only after the clinical need for them has ended. In addition, a stent should also be capable of satisfying the mechanical requirements discussed above during the desired treatment time.

In general, it is desired that a biodegradable stent maintain its mechanical stability during a desired treatment period. However, some erodible metals degrade much faster than a desired treatment time. In addition, if a stent erodes too quickly, large pieces of the stent may detach from the eroding stent and cause embolization in a vessel. In addition, polymers that exhibit a high degree of bulk eroding behavior can experience a substantial deterioration in mechanical properties that could lead to failure prior to the end of the treatment period. Therefore, there is a need to control erosion of biodegradable stents to maintain structural stability.

SUMMARY OF THE INVENTION

Certain embodiments of the present invention may be directed to an implantable medical device that may include a bioabsorbable polymeric substrate region and a bioabsorbable polymeric coating region above the substrate region. The coating region may have a lower average erosion rate or a longer half-life than the substrate region.

Other embodiments of the present invention may be directed to an implantable medical device that may include a bioabsorbable substrate region and a coating region above the substrate region for controlling erosion of the substrate region. The coating region may include a bioabsorbable polymer and a nonbioactive pore forming agent dispersed or mixed within the bioabsorbable polymer.

Some embodiments of the present invention may be directed to an implantable medical device including a bioabsorbable substrate region and a coating region above the substrate region. The coating region may include a porous bioabsorbable polymeric matrix that allows transport of bodily fluids through pores of the porous matrix to the substrate region.

Additional embodiments of the present invention may be directed to a method of fabricating an implantable medical device including forming a bioabsorbable coating region above a bioabsorbable substrate region. The coating region may be configured to limit exposure of the substrate region to bodily fluids. The method may further include forming pores in the coating region. The pores may be configured to allow diffusion of the bodily fluids to the substrate region.

Certain other embodiments of the present invention may be directed to a method of forming a bioabsorbable coating region over a bioabsorbable substrate region. The coating region may be configured to reduce, inhibit, or delay erosion of the substrate region. The method may include controlling a thickness of the coating region to allow a specified amount of erosion of the substrate region during a selected time period.

Further embodiments of the present invention may include a method of forming a bioabsorbable coating region over a bioabsorbable substrate region, the coating region being configured to reduce, inhibit, or delay erosion of the substrate region. The method may include controlling a degree of crystallinity of the coating region to allow a specified amount of erosion of the substrate region during a selected time period.

DETAILED DESCRIPTION OF THE INVENTION

The term "implantable medical device" is intended to include, but is not limited to, self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The structural pattern of the device can be of virtually any design.

Figure 1:
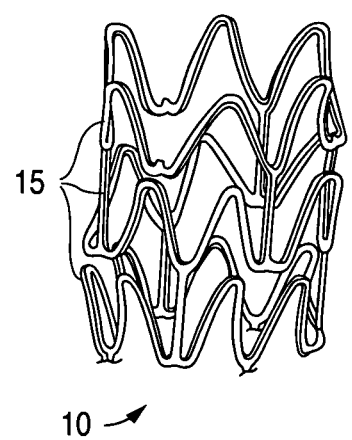
FIG. 1 depicts an example of a stent.

A stent, for example, may include a pattern or network of interconnecting structural elements or struts. FIG. 1 depicts a three-dimensional view of a stent 10 which shows struts 15. The pattern shown in FIG. 1 should not be limited to what has been illustrated as other stent patterns are easily applicable with the method of the invention. A stent such as stent 10 may be fabricated from a tube by forming a pattern with a technique such as laser cutting or chemical etching.

Various embodiments of the present invention relate to biodegradable implantable medical devices that include biodegradable coatings over a biodegradable substrate. The substrate may be, for example, struts as shown in FIG. 1. For stents made from biodegradable materials, the stent may be intended to remain in the body for a duration of time until its intended function of, for example, maintaining vascular patency and/or drug delivery is accomplished. The duration can be in a range from about a month to a few years. However, the duration is typically in a range from about six to twelve months. For biodegradable polymers used in coating applications, after the process of degradation, erosion, absorption, and/or resorption has been completed, no polymer will remain on the stent. In some embodiments, very negligible traces or residue may be left behind.

A variety of methods of coating can be used in practicing the present invention including, but not limited to, spraying, dipping, brushing, pouring, dripping, spinning, roller coating, meniscus coating, powder coating and various inking approaches such as inkjet-type application. In some embodiments, the method of coating is spraying. In other embodiments, additional process steps are necessary such as, for example, the application of heat or energy to the implantable medical device and/or coating.

Embodiments of the coatings described herein may be configured to reduce the overall rate of erosion, or more generally, control erosion of the substrate during a desired treatment period. Thus, the substrate may be allowed to maintain its mechanical strength in order to serve the purpose of maintaining vascular patency.

Additionally, reducing the rate of erosion of the substrate may prevent large pieces of the stent from detaching from the eroding stent and causing embolization in a vessel. Ideally, it is desirable for a substrate to maintain mechanical stability during a desired treatment period and then to degrade quickly without detachment of large pieces of the stent after the treatment period.

One preferred type of erosion profile in treatments involving struts of biodegradable stents may be separated into two time periods. An initial period may include a slow or minimal degradation for as long as mechanical support for the vessel is desired. The slow degradation may then be followed by a period of rapid degradation occurring approximately after the stent is no longer required. A stent configuration that may achieve such a profile may include a slow eroding, flexible outer region (e.g., a coating) and a fast eroding, stiff, strong inner region (a strut substrate) that provides mechanical support as long as support is desired.

Additionally, other factors to consider in stent design are form factor and radio-opacity for viewing a stent during and after deployment. It is generally desirable for a stent to have low form factor (e.g., thinner struts) to reduce bodily fluid flow disruption in tend not to be radiopaque. In addition, in order to have adequate strength, the struts may be significantly thicker than struts in metal stents. For example, a polymer-fabricated stent composed of poly(L-lactic acid) may require struts more than 50% thicker than a metallic stent. On the other hand, a metallic stent fabricated from a bioerodible metal, such as magnesium, erodes too quickly to remain intact for the typical treatment time of six to twelve months.

As discussed above, polymers can be biostable, bioabsorbable, biodegradable, or bioerodible. Biostable refers to polymers that are not biodegradable. The terms biodegradable, bioabsorbable, and bioerodible, as well as degraded, eroded, and absorbed, are used interchangeably and refer to polymers that are capable of being completely eroded or absorbed when exposed to bodily fluids such as blood and can be gradually resorbed, absorbed and/or eliminated by the body.

Several characteristics or parameters of the degradation process are important in designing biodegradable devices. These include an average erosion rate of a device, the erosion profile, the half-life of the degrading polymer, and mechanical stability of a device during the degradation process.

The "average erosion rate" may be an average erosion rate over any selected time interval:

$$\text{Average erosion rate} = (m_2 - m_1)/(t_2 - t_1)$$

where "m" refers to mass of the device, "t" refers to a time during erosion, and $m_1$ and $m_2$ are the masses of the device at $t_1$ and $t_2$ during erosion. For instance, the selected time interval may be between the onset of degradation and another selected time. Other selected times, for example, may be the time for about 25%, 50%, 75%, or 100% (complete erosion) of the device to erode. Complete erosion may correspond approximately to the time required for treatment by the device.

The "half-life" of a degrading polymer refers to the length of time for the molecular weight of the polymer to fall to one half of its original value. See e.g., J. C. Middleton and A. J. Tipton, Biomaterials, Vol. 21 (23) (2000) pp. 2335-2346.

An "erosion profile" refers to the functional dependence of the instantaneous erosion rate on time. In terms of the erosion profile, biodegradable polymers span a continuum from polymers having a relatively constant instantaneous erosion rate with time during a degradation process to polymers with an instantaneous erosion rate that is strongly dependent on time. The former case corresponds to surface eroding polymers, while the latter case refers to bulk eroding polymers. The concepts of surface eroding and bulk eroding are limiting extremes. Real systems typically behave somewhere in between surface erosion and bulk erosion.

Biodegradation of polymers generally refers to changes in physical and chemical properties that occur in a polymer upon exposure to bodily fluids as in a vascular environment. The changes in properties may include a decrease in molecular weight, deterioration of mechanical properties, and decrease in mass due to erosion or absorption. Mechanical properties may correspond to strength and modulus of the polymer. Deterioration of the mechanical properties of the polymer decreases the ability of a stent, for example, to provide mechanical support in a vessel. The decrease in molecular weight may be caused by, for example, hydrolysis and/or metabolic processes. Hydrolysis is a chemical process in which a molecule is cleaved into two parts by the addition of a molecule of water.

Consequently, the degree of bulk degradation of a polymer is strongly dependent on the diffusivity, and hence the diffusion rate of water in the polymer. In general, the "diffusion rate" or flux, "J," of a species in a material is defined as the number of randomly moving molecules that pass through a unit area per second. The diffusivity, "D," is the constant of proportionality between the flux of a species and the concentration gradient $\partial C/\partial x$, along a coordinate x, as given by Fick's first law of diffusion: $J = -D(\partial C/\partial x)$. The value of D varies with temperature according to an Arrhenius-type equation: $D = D_0 \exp[-Q/RT]$, where $D_0$ is a material constant and Q is the activation enthalpy for diffusion.

As a bulk eroding polymer erodes, a decrease in molecular weight of the polymer can result in deterioration of mechanical properties and contributes to erosion or absorption of the polymer into the bodily fluids. Therefore, the time frame of degradation of a polymer part is dependent on water diffusion, hydrolysis, decrease in molecular weight, and erosion.

Alternatively, a surface eroding polymer typically has relatively low water diffusivity. As a result, surface erosion is a heterogeneous process in which degradation and erosion tend to occur at or near a surface of the polymer exposed to the bodily fluids.

In many treatment situations, a surface eroding erosion profile is more desirable since the disintegration of the device occurs less abruptly than for a bulk eroding polymer. A more gradual release of degraded material in a vascular system has a lower risk of embolization caused by a piece of the device breaking away. A surface eroding polymer also tends to delay, inhibit, or prevent degradation of regions or layers below a surface eroding layer or region. Additionally, a surface eroding polymer may be preferable because there tends to be little or no change in mechanical properties of remaining polymer that has not eroded. However, a device composed of a surface eroding polymer may still tend to weaken as it loses mass. In some embodiments, one or more coating regions composed of bulk eroding polymers over a bulk eroding or fast eroding substrate region (such as an erodible metal) can simulate the erosion profile of a surface eroding polymer.

Furthermore, as indicated above, polymer erosion spans a continuum from bulk eroding to surface eroding. Bulk erosion refers to degradation of a polymer substantially throughout the bulk of a polymer part exposed to bodily fluids. As indicated above, in bulk erosion the instantaneous absorption or erosion rate is strongly dependent on time. The erosion profile of bulk eroding polymers (see FIG. 2) typically consists of a relatively slow instantaneous erosion rate for a period of time after initial exposure to bodily fluids followed by a sharp increase in the instantaneous erosion rate.

The degradation behavior of a polymer is strongly linked to the diffusivity of water in the polymer. As the diffusivity of water increases in a polymer, the bulk eroding behavior of the polymer increases. A bulk eroding polymer may be capable of absorbing less than about 3% by weight, or more narrowly, less than about 1% by weight. Water diffusivity in the polymer increases as the polymer region degrades.

Figure 2:
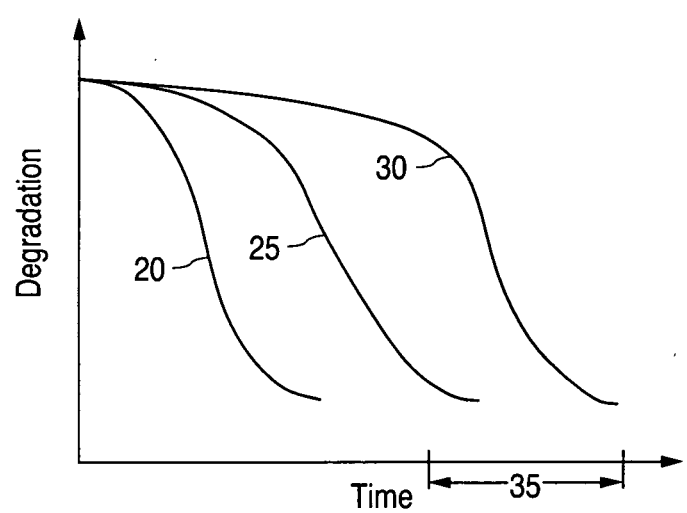
FIGS. 2 and 3 depict degradation as a function of time for a polymer.

For a bulk eroding polymer, the molecular weight loss, deterioration of mechanical properties, and erosion tend to occur sequentially over different time frames. FIG. 2 illustrates degradation as a function of time for a bulk eroding polymer part. A curve 20 represents the decrease in molecular weight that occurs within the bulk of the polymer material. The decrease in molecular weight causes deterioration in mechanical properties of the polymer, which is shown by a curve 25. A curve 30 represents the cumulative erosion versus time of the polymer. Some bulk eroding polymers, may exhibit relatively little erosion even with a substantial loss of molecular weight and deterioration of mechanical properties, as depicted in FIG. 2. For such polymers, much of the erosion may occur over a relatively short time frame, as in a time period 35.

Representative examples of bulk eroding polymers include, but are not limited to, poly(L-lactide), poly(glycolide), poly(D,L-lactide), poly(trimethylene carbonate), polycaprolactone, and copolymers thereof. During a course of treatment with a biodegradable polymeric stent, the polymer degrades resulting in a decrease in the molecular weight of the polymer and deterioration of mechanical properties.

In contrast to bulk erosion, the instantaneous absorption or erosion rate of a surface eroding polymer (see FIG. 3) is constant or relatively constant with time. This erosion behavior is due to the fact that surface erosion is a heterogeneous process in which degradation and erosion tend to occur at or near a surface of the polymer exposed to the bodily fluids. For a surface eroding polymer, changes in the various properties may occur over the same or similar time frames since degradation is limited to a region at or near an exposed surface.

Figure 3:
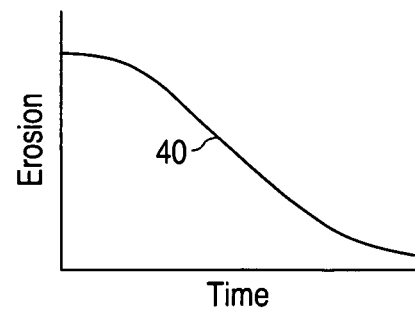

In FIG. 3, a curve 40 depicts the cumulative erosion as a function of time for a surface-eroding polymer part. The erosion rate is dependent on the surface area of the eroding part. Since degradation is heterogeneous, the decrease in molecular weight and deterioration of the mechanical properties occur at or near the surface of a surface-eroding polymer part. In the bulk of the polymer part or away from the surface of a surface-eroding polymer part, the molecular weight and mechanical properties are unchanged or substantially unchanged. Representative examples of surface eroding polymers include, but are not limited to, polyorthoesters, polyanhydrides and copolymers thereof.

Representative examples of polymers that may be used to fabricate an implantable medical device using the methods disclosed herein include, but are not limited to, poly(N-acetylglucosamine) (Chitin), Chitoson, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating an implantable medical device according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

Additionally, some metals are considered bioerodible since they tend to erode or corrode relatively rapidly when exposed to bodily fluids. Biostable metals refer to metals that are not bioerodible. Biostable metals have negligible erosion or corrosion rates when exposed to bodily fluids. In general, metal erosion or corrosion involves a chemical reaction between a metal surface and its environment. Erosion or corrosion in a wet environment, such as a vascular environment, results in removal of metal atoms from the metal surface. The metal atoms at the surface lose electrons and become actively charged ions that leave the metal to form salts in solution.

Representative examples of biodegradable metals that may be used to fabricate an implantable medical device may include, but are not limited to, magnesium, zinc, and iron. In one embodiment, a bioerodible metal stent may be completely eroded when exposed to bodily fluids, such as blood, between about a week and about three months, or more narrowly, between about one month and about two months.

As discussed above, it is advantageous to control the erosion rate of a stent having a biodegradable substrate. The erosion rate of the substrate may be controlled by reducing or limiting exposure of the substrate to bodily fluids of the vascular environment. Embodiments of implantable medical devices described herein may include a biodegradable coating region above a biodegradable substrate region. "Above" a region is defined as higher than or over a region measured along an axis normal to a region, but not necessarily in contact with the region. The coating region may be configured to control the average erosion rate of the substrate region by controlling exposure of the substrate region to bodily fluids. The exposure of the portions of the substrate regions below the coating region is influenced by the transport of bodily fluids through the coating region to the substrate region.

Thus, embodiments of the implantable medical device may include relatively distinct regions that have different erosion profiles when exposed to bodily fluids. In this way the erosion profile of the stent may be customized to various treatments.

Embodiments may include a substrate region that is metallic, a bulk eroding polymer, or a substantially or completely surface eroding polymer. Additionally, the coating region may include a bulk eroding polymer or a substantially or completely surface eroding polymer.

In certain embodiments, the substrate region may be a radially expandable stent including a pattern of struts. The cross-sectional shape of the struts can be circular, square, rectangular, oval, or any other shape. For example, a metallic substrate may be a cylindrical or substantially cylindrical coil or mesh of metallic wire. In addition, a metallic substrate may be a pattern of struts formed on a metallic tube by cutting or etching.

In some embodiments, the coating region may include a bioactive agent. A "bioactive agent" is a moiety that is mixed, blended, bonded or linked to a polymer coating, or to a polymer from which a stent is made, and provides a therapeutic effect, a prophylactic effect, both a therapeutic and a prophylactic effect, or other biologically active effect upon release from the stent. The bioactive agents of the present invention may remain linked to a portion of the polymer or be released from the polymer. For the purpose of embodiments of the present invention, a bioabsorbable polymer and the degradants of bioabsorbable polymers tend not to provide a therapeutic effect, a prophylactic effect, both a therapeutic and a prophylactic effect, or other biologically active effect upon release from the stent.

The polymer region may be configured to release the active agent for a selected amount of time. The release may occur through the break-up of the polymer and/or via migration of the active agent out of the polymer. The selected amount of time may correspond approximately to a desired treatment time of a stent. Additionally, the substrate region may have pores that are configured to include an active agent. For example, the metallic region can be formed by sintering particles, fibers, and wires of material.

In some embodiments, the substrate region may have a faster average erosion rate or lower half-life when exposed to bodily fluids than the coating region when exposed to bodily fluids. The coating region may be configured to delay, inhibit, or prevent erosion of the substrate region in a manner that allows the substrate region to provide mechanical support to a bodily lumen. For example, the coating region may be configured to delay, inhibit, or prevent erosion of the substrate region for a selected time period. The selected time period may be at least a portion of the time period that the substrate region is desired to provide mechanical support. It may be desirable for a substrate region to provide mechanical support for a majority of, all of, or longer than a desired treatment time of the stent.

In other embodiments, the substrate region may erode when the substrate region is exposed to bodily fluids due to degradation of the coating region. The substrate region may be exposed to bodily fluids by complete erosion of the coating region over a portion of the substrate region and/or diffusion of bodily fluids through the coating region. Thus, a substrate region may start to erode when the coating region is only partially degraded and/or eroded. Partially means less than 50% of the coating, or alternatively less than 40%, 30%, 20%, 10%, or 5%. In other embodiments, the substrate region may start to erode when the coating region is completely (greater than 99%) degraded and/or eroded or when a majority of the coating is degraded and/or eroded. Majority includes over 50%, 60%, 70%, 80%, 90%, or alternatively, over 95% of the coating region As indicated above, the diffusion rate of water in a bulk eroding polymer is relatively high. Therefore, a coating region composed of a bulk eroding polymer may allow a substantial amount of bodily fluids to diffuse through the coating and erode the substrate region. The substrate region may be completely or almost completely eroded before the coating region is completely eroded.

In bulk eroding polymers, water diffusivity in the polymer increases as the polymer region degrades. Therefore, the rate of erosion of the substrate region may increase as the device erodes. The increased diffusivity of water may result in substantial erosion of the substrate region prior to complete erosion of the polymer region. The coating region may completely or almost completely erode before the substrate region is completely eroded.

In other embodiments, a coating region may be a surface eroding polymer or a substantially surface eroding polymer. A surface eroding polymer may be selected that has a water diffusivity that inhibits or prevents erosion of the substrate region for a selected time period. The substrate region may be configured to erode when erosion of the polymer region exposes a portion of the substrate region to bodily fluids. Thus, due to higher water diffusivity in a bulk eroding polymer, it is expected that the erosion of the substrate region will occur later and over a smaller time frame (more abruptly) with a bulk eroding polymer as a coating region than with a surface eroding polymer as a coating region.

Figure 4:
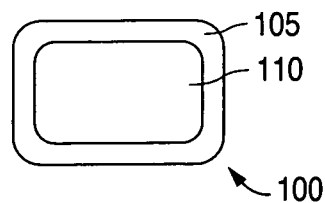
FIG. 4 depicts a schematic illustration of a cross-section of a strut.

FIG. 4 depicts a schematic illustration of an embodiment of a cross-section of a strut 100 of a stent that includes a coating region 105 and a substrate region 110. Coating region 105 is composed primarily of a biodegradable polymer. Substrate region 110 can be an erodible metal or a biodegradable polymer.

Figure 5:
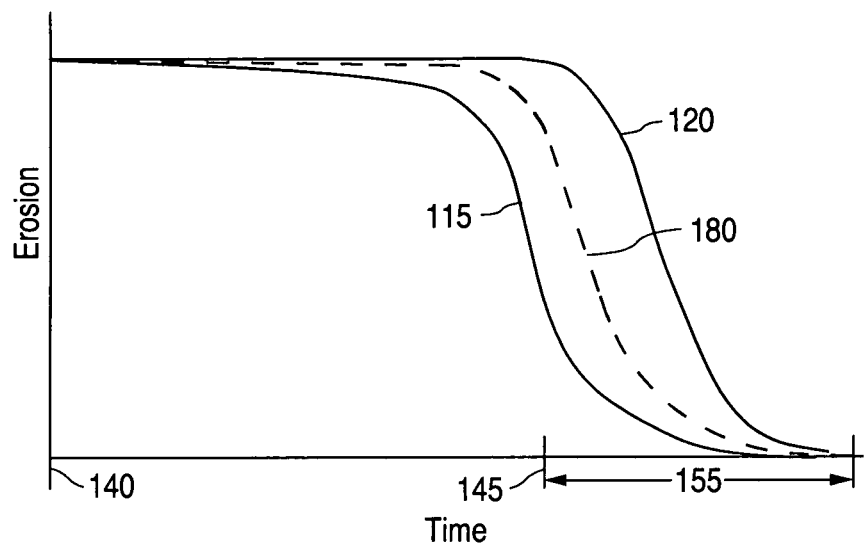
FIGS. 5 and 6 depict erosion profiles of a stent.
Figure 6:
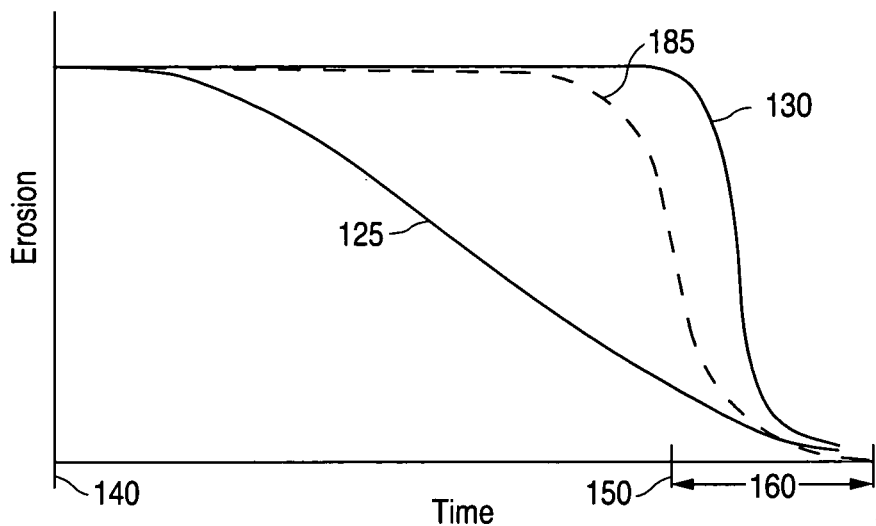

FIGS. 5 and 6 illustrate examples of erosion as a function of time for such a stent. FIG. 5 depicts erosion for a stent with a bulk eroding coating region. In FIG. 5, a curve 115 represents the cumulative erosion vs. time of the coating region and curve 120 represents the cumulative erosion of the substrate region. From the shape of curve 120, the substrate region may be a fast eroding metallic region or bulk eroding polymer.

FIG. 6 depicts erosion for a stent with a coating region 105 composed of a substantially surface eroding polymer. In FIG. 6, a curve 125 represents the cumulative erosion vs. time of the coating region and a curve 130 represents the cumulative erosion vs. time of the substrate region.

In FIGS. 5 and 6, a time 140 corresponds to an approximate time of implantation of the stent in a vessel. From time 140 to approximately a time 145 in FIG. 5 and between time 140 and approximately time 150 in FIG. 6, there is minimal erosion of the substrate region. In FIG. 5, time 145 represents the onset of substantial erosion of the substrate region with a bulk eroding polymer coating region. Similarly in FIG. 6, time 150 represents the onset of substantial erosion of the substrate region with a surface eroding polymer coating region. Coating region 105 delays the onset of substantial erosion to a later time as compared to a strut with no coating region.

At some time during a time period 155 in FIG. 5 and a time period 160 in FIG. 6, the stent may be no longer required for treatment. During time periods 155 and 160, the coating and substrate regions may be completely or almost completely eroded and the substrate regions may no longer provide mechanical support.

The erosion of the substrate region rises sharply during time periods 155 and 160 due to degradation and/or erosion of the coating regions. A comparison of curve 120 to curve 130 illustrates the sharper erosion profile of the substrate when a surface eroding polymer is used rather than a bulk eroding polymer for the coating region. Curve 120 is less steep than curve 130 because the diffusion of water in the bulk eroding polymer coating is substantially greater than through a surface eroding polymer coating. The substrate region with the bulk eroding polymer coating is exposed to a substantial amount of bodily fluids prior to complete erosion of the coating from a portion of the substrate region, i.e, prior to direct exposure of the substrate region to bodily fluids.

Thus, FIGS. 5 and 6 illustrate qualitatively how the coating region alters the erosion profile of the substrate region. In particular, the coating region alters the approximate time of the onset of erosion (time 145 in FIG. 5 and time 150 in FIG. 6) and the subsequent time period of substantial erosion (time period 155 in FIG. 5 and time period 160 in FIG. 6). Additionally, the rate of erosion (the slope of the erosion profiles) is also altered.

Thus, the coating region may be configured to control exposure of the substrate region to bodily fluids and achieve a specified degree of erosion of the substrate region. There are several properties of a coating region that may be used to alter or control the exposure of the substrate region, and hence, its erosion profile.

The thickness of the coating region is directly related to the times of the onset of erosion and a time period of substantial erosion. Increasing the thickness of the coating region alters the erosion profile of the substrate region primarily by increasing the time for water to diffuse through a coating region to the substrate region. As illustrated by Fick's first law of diffusion, as the thickness increases, the flux of fluid diffusing through the coating increases. The time for complete erosion of the coating region over a portion of the substrate region is also altered. For instance, time periods 155 and 160 are shifted to later times as the thickness of the coating region increases.

In some embodiments, the thickness of the coating region may be controlled to control erosion of the substrate region. In one embodiment, a method may include controlling a thickness of the coating region to allow a specified amount of erosion of the substrate region during a selected time period. For example, the specified amount of erosion may be an amount of erosion that allows the substrate region to maintain mechanical support to a bodily lumen. In other embodiments, the specified amount of erosion may be 10%, 40%, 60%, 80%, or 90% of the amount of erosion that renders the substrate region unable to continue to support a bodily lumen.

As indicated above, the erosion profile of the substrate region is also altered by changing the diffusion rate or flux of bodily fluids or water through the coating region. In one embodiment, the diffusion rate of water may be changed by modifying the chemical composition of the coating region, e.g., by using a different polymer. As discussed above, the bulk eroding polymers discussed above tend to have relatively high water diffusivities and the surface eroding polymers have relatively low water diffusivities.

Additionally, another way of changing the diffusion rate of water in the coating region is to introduce porosity into the coating region. Introducing porosity into a coating region allows variation of the erosion profile of the substrate region without substantially changing the chemical composition of the coating region. This may be an advantage since there may be reasons other than diffusion rate of water in a coating material to use a particular coating composition, e.g., biocompatibility, processing issues, etc.

A porous coating is also desirable because the pores facilitate transport of eroded material out of a stented area. A build-up of eroded material within a coating may inhibit transport of water through a coating, and thus, inhibit degradation. Increasing removal of eroded material increases the diffusion of water through the coating, and thus the degradation rate.

Furthermore, the erosion profile of the coating region, and consequently the substrate region, may be tuned or modified in various ways. Introducing porosity into a coating region composed of a polymer with bulk eroding properties may tend to increase the average erosion rate or decrease the half life of the substrate region. For example, curve 180 in FIG. 5 and curve 185 in FIG. 6 may represent the erosion profiles of the substrate region when the coating region has porosity.

In some embodiments, a layer is "porous" when it has a void-to-volume percentage that ranges from about 40% to about 90%, from about 70% to about 80%, or any range therein. In some embodiments, a layer is "non-porous" when it has a void-to-volume percentage that ranges from about 0% to about 5%, from about 1% to about 3%, or any range therein.

The "void-to-volume percentage" is defined as the volume of the pores divided by the total volume of the layer including the volume of the pores. In some embodiments, the void-to-volume percentage can be measured using standard test method BSR/AAMI/ISO 7198, which has been adopted in-whole as a revision of ANSI/AAMI VP20-1994 (Cardiovascular Implants—Vascular Prosthesis section 8.2.1.2, Method for Gravimetric Determination of Porosity, Am. Nat'l Stds. Inst./Assoc. for the Adv. of Med. Instr.)

Various embodiments of an implantable medical device may include a coating region that includes a porous bioabsorbable matrix above a substrate region. "Above" a region is defined as higher than or over a surface or layer measured along an axis normal to a surface, but not necessarily in contact with the surface or layer. In some embodiments, the polymeric matrix may allow transport of bodily fluids through pores of the porous matrix to the substrate region. Porosity can be introduced in the coating region by any method known to one of skill in the art.

In one embodiment, the porous matrix may be formed by phase inversion precipitation of a bioabsorbable polymer. By way of example, a polymer may be mixed with two miscible solvents to form a solution. One of the solvents (solvent A) should be less volatile than the other solvent (solvent B). Additionally, the polymer should be less soluble in solvent A. The solution can then be applied to a portion of the surface of the implantable medical device. Next, when the solvents are allowed to evaporate, the polymer slowly precipitates as solvent B is essentially removed from the coating. As a result, after complete drying, the polymer matrix becomes porous.

One of ordinary skill in the art will understand that the size of the pores can be controlled by the choice of polymers and solvents and the relative concentrations of the solutions. The depth of a porous matrix into the coating region can be controlled by using the phase inversion technique after a portion of the coating region has been applied to the surface of the device. Pores in the range of about 0.1 microns to about 1 micron in diameter may be suitable.

In other embodiments, the porous matrix can be formed by using a sintering process. Sintering is a process of fabrication where particles are bonded together by partially melting some of the particles. For example, a bioabsorbable polymeric powder or particles can be applied to the surface of the device and then pressed together. The particles can be about 1 micron to about 10 microns. Then, the polymeric particles can be heated to temperatures slightly below or about the melting point of the polymer. Without entirely melting all of the particles, the particles bond to each other at their respective surfaces. Space remains between the lattice of the particles to form porous cavities.

In certain embodiments, a coating region including a bioabsorbable polymeric porous matrix may be formed with a pore forming agent or porogen. The coating region may include a bioabsorbable polymer and a pore forming agent dispersed or mixed within the bioabsorbable polymer. In one embodiment, a pore forming agent in the form of particles and/or fibers, for example, may be added to a polymeric material used to form a coating region of an implantable medical device. Pores within the polymeric material of the coating region may be formed when at least a portion of the pore forming agent is dissolved or eroded by a fluid. The fluid may be a suitable solvent (e.g., water) or bodily fluids that dissolve or erode the pore forming agent. In some embodiment, a tortuous porous network may be formed in the coating region that allows diffusion of bodily fluids to the substrate region.

In an embodiment, pores may be formed in the coating region through dissolution and/or erosion of at least some of the pore forming agent after exposure of the coating region to a solvent in vitro. Alternatively or additionally, pore forming agent may be removed through dissolution and/or erosion of the pore forming agent when the coating region is exposed to bodily fluids after implantation of the device.

Various non-bioactive pore forming agents may include, but are not limited to, salts, sugars, and water-soluble polymers. Water-soluble polymers may include, for example, polymeric salts, polyvinyl alcohol, polyethylene glycol, polyethylene oxide, glucose, dextran, dextrose, lactose, gamma globulin, ambumin, and combinations thereof. Such particles may be removed in vivo, for example, by washing in water or a very dilute acid bath. Examples of non-polymeric salts include, but are not limited to, sodium chloride, phosphate salts, carbonate salts, sodium bicarbonate, and combinations thereof. Other pore forming agents may include urea and amino acids.

As described above, the coating region may include a bioabsorbable polymer and a pore forming agent dispersed or mixed within the bioabsorbable polymer. In some embodiments, the pore forming agent may include a second bioabsorbable polymer mixed, dispersed, or blended within the coating region. The second bioabsorbable polymer may be in the form of particles and/or fibers. It is desirable for the second bioabsorbable polymer to have a higher average erosion rate or a shorter half-life than the bioabsorbable polymer of the coating region. Thus, the coating region may include a continuous phase of a slower eroding bioabsorbable polymer and a dispersed phase of a faster eroding bioabsorbable polymer.

In an embodiment, a pore formation rate after implantation may be tuned by selecting a second bioabsorbable polymer with a particular average erosion rate or half life. In a similar manner, some embodiments may include a pore forming agent that includes an erodible metal mixed or dispersed with the coating region.

Furthermore, properties of the porous matrix of the coating region may influence the erosion profile of the coating region, and hence, the erosion profile of the substrate region. Such properties of the porous matrix include, but are not limited to, the pore size distribution and porosity. Porosity may be defined as the ratio of the void volume to the total volume of the coating region. In some embodiments, the erosion profile of the coating region and/or substrate region may be tuned or controlled by controlling the pore size distribution and porosity of the coating region.

The pore size distribution and porosity depend on variables including, but not limited to, the number concentration of particles and/or fibers (number of particles and/or fibers per unit volume) of pore forming agent and the particle and/or fiber size of pore forming agents. Thus, the pore size distribution porosity can be controlled by screening the particles and/or fibers according to size and adding particles of a predetermined size to the materials. For example, increasing the particle size of pore forming agent tends to increase both the porosity and pore size distribution. In addition, increasing the number concentration of particles tends to increase the porosity.

Figure 7:
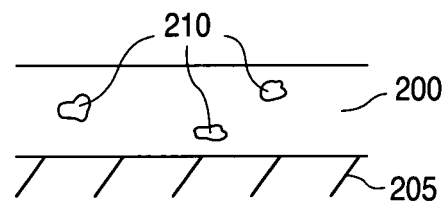
FIGS. 7 and 8A depict a schematic illustration of a pore forming agent in a coating region.
Figure 8A:
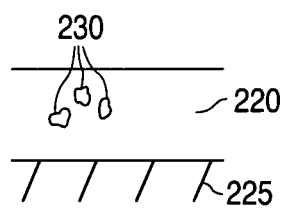
Figure 8B:
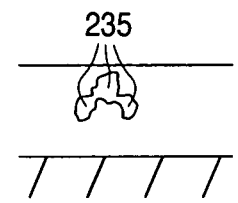
FIG. 8B depicts a schematic illustration of pores formed in a coating region.

FIGS. 7 and 8A-B illustrate that variables such as particle size and concentration can influence the characteristics of a porous network formed by pore forming agents. FIG. 7 depicts a portion of a coating region 200 over a substrate region 205. Coating region 200 has a relatively low concentration of particles 210 of pore forming agent. At relatively low concentrations, of particles 210 may be dissolved or eroded by fluid (solvent or bodily fluids) to form isolated pores or voids that are not connected by other pores.

Alternatively, FIG. 8A depicts a coating region 220 over a substrate region 225 with a relatively high concentration of particles 230 of pore forming agent. For a majority of particles 230, the distances between neighboring particles are smaller than distances between neighboring particles for a majority of particles 210. As illustrated in FIG. 8B, it is expected that if the concentration of particles 230 is high enough, as particles 230 dissolve or erode, interconnected pores or voids 235 are formed. Thus, a tortuous porous network may be formed in the coating region.

It is believed that the formation of a porous network tends to occur in a relatively short time frame. It is expected that the diffusion rate or flux of fluid through the coating region may be relatively constant after initial exposure to fluid. After formation of an interconnected porous network, the diffusion rate of fluid may tend to increase substantially during a short time frame. Thus, in some embodiments, the concentration of pore forming particles can be tuned to obtain a desired time of formation of the interconnected network after exposure of the coating region to bodily fluids.

Additionally, the diffusion rate or flux of fluid within a coating region may also be controlled through selection of the chemical properties of the pore forming agent, in particular, the osmotic behavior of water soluble pore forming agents. "Osmosis" refers to the diffusion of molecules from a region of higher concentration of an osmotically active agent to a place of lower concentration until the concentration in both regions is equal.

"Osmotic pressure" is the pressure exerted by a solution necessary to prevent osmosis into that solution when it is separated from the pure solvent by a semipermeable membrane that allows diffusion of only the solvent. An osmotically active agent dispersed in the coating region may increase the osmotic pressure differential between the coating region and fluid regions adjacent to the coating region.

Therefore, increasing the concentration of the osmotically active agents in the coating region increases the osmotic pressure differential which results in increased diffusion of water or bodily fluids into the coating region. The increased diffusion rate may then increase the degradation rate of the coating region. The osmotic pressure differential tends to drive fluid into the pores or voids formed by dissolution of particles or pore forming agent.

It is expected that a pore forming agent with a higher osmotic pressure may tend to result in formation of a coating region with a larger pore size distribution and a greater porosity. Thus, in some embodiments, the pore size distribution and porosity of a coating region may be controlled by selection of a pore forming agent based on its osmotic pressure.

In some embodiments, the diffusion rate of bodily fluids, and hence the erosion of the substrate region, may be controlled with the degree of crystallinity of a bioabsorbable polymeric coating region. An embodiment of a method of fabricating an implantable medical device may include controlling a degree of crystallinity of the coating region to allow a specified amount of erosion of the substrate region during a selected time period.

In general, the diffusion rate of a fluid through a polymer decreases as the degree of crystallinity increases. Therefore, it is expected that the diffusion rate of water and bodily fluids is lower in crystalline and semi-crystalline polymers than in amorphous polymers. Thus, in an embodiment, the erosion rate of a substrate region may be controlled by modifying the degree of crystallinity of the coating region.

In one embodiment, the crystallinity of a polymer may be modified by heating the polymer. Heating a polymer can alter the degree of crystallinity and/or size of crystalline regions in a polymer material. The degree of crystallinity may be altered by heating the polymer to within a particular temperature range. Heating a polymer material to a temperature below the glass transition temperature, $T_g$, of the polymer does not significantly alter the molecular structure, and hence, the mechanical properties of the material. Below $T_g$, energy barriers to segmental motion of the chains of a polymer inhibit or prevent alteration of molecular structure of a polymer material.

In general, crystallization may occur in a polymer material that is heated to a temperature between $T_g$ and the melting temperature, $T_m$, of the polymer. As a result, heating a polymer to a temperature between the $T_g$ and the $T_m$ of the polymer increases the modulus of the polymer.

Figure 9:
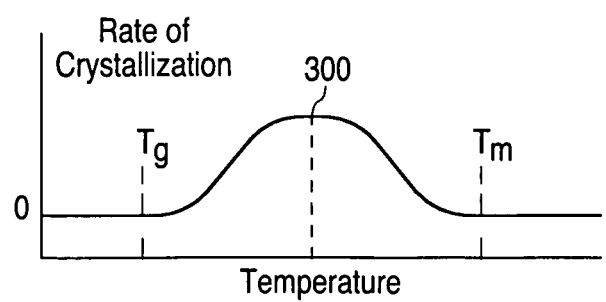
FIG. 9 depicts a schematic plot of the rate of crystallization of a polymer as a function of temperature.

FIG. 9 depicts a schematic plot of the rate of crystallization of a polymer as a function of temperature. (Rodriguez, F., *Principles of Polymer Systems*, $2^{nd}$ ed., McGraw Hill (1982)) FIG. 9 shows that the rate of polymer crystallization increases as the temperature is increased from below the $T_g$ of the polymer or is decreased from above the $T_m$ of the polymer. The rate of crystallization reaches a maximum 300 somewhere between the $T_g$ and the $T_m$. FIG. 9 shows that effectively no crystallization occurs below the $T_g$ or above the $T_m$.

In addition, as indicated above, an amorphous polymer may be formed by heating a polymer material. Above the $T_m$, a polymer material is a disordered melt and cannot crystallize and any crystallinity present is destroyed. Quenching a polymer heated to above the $T_m$ to a temperature below the $T_g$ of the polymer may result in the formation of a solid amorphous polymer. The resulting amorphous polymer material may have a lower modulus and be a more flexible or a less stiff material than before heating.

A coating region may be heated in a variety of ways including, but limited to heating in an oven or blowing hot air on the coating. A coating may be quenched, for example, in a water bath.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent comprising:
   at least one bioerodible metal strut; and
   a coating coated around and contacting the at least one bioerodible metal strut, the coating comprising a bioabsorbable polymer and particles or fibers of a nonbioactive erodible metal pore-forming agent dispersed or mixed within the bioabsorbable polymer; wherein the at least one bioerodible metal strut has a faster average erosion rate when exposed to bodily fluids than the coating when exposed to the bodily fluids; wherein the at least one bioerodible metal strut is configured to start to erode when the coating is partially degraded after the stent is implanted in a vascular lumen; and wherein the at least one bioerodible metal strut is configured to completely or almost completely erode before the coating is completely eroded.

2. The stent of claim 1, wherein the at least one bioerodible metal strut comprises magnesium, zinc, iron or a combination thereof.

* * * * *